US008805465B2

(12) United States Patent
Hodge et al.

(10) Patent No.: US 8,805,465 B2
(45) Date of Patent: Aug. 12, 2014

(54) MULTIPLE SENSOR ASSEMBLIES AND CABLES IN A SINGLE SENSOR BODY (75) Inventors: Michelle L. Hodge, Longmont, CO (US); Casey V. Medina, Westminster, CO (US); Paul D. Mannheimer, Danville, CA (US)

(73) Assignee: Covidien LP, Mansfield, MA (US)

( * ) Notice: Subject to any disclaimer, the term of this patent is extended or adjusted under 35 U.S.C. 154(b) by 699 days.

(21) Appl. No.: 12/956,943

(22) Filed: Nov. 30, 2010

(65) Prior Publication Data
US 2012/0136223 A1 May 31, 2012

(51) Int. Cl.
A61B 5/1455 (2006.01)

(52) U.S. Cl.
USPC .......................................... 600/344; 600/310

(58) Field of Classification Search
USPC .................. 600/310, 322, 323, 344
See application file for complete search history.

(56) References Cited

U.S. PATENT DOCUMENTS

| 5,088,493 | A | 2/1992 | Giannini et al. |
| 5,218,962 | A | 6/1993 | Mannheimer et al. |
| 5,497,769 | A | 3/1996 | Gratton et al. |
| 5,772,587 | A | 6/1998 | Gratton et al. |
| 5,827,182 | A | 10/1998 | Raley et al. |
| 5,983,122 | A | 11/1999 | Jarman et al. |
| 6,192,261 | B1 | 2/2001 | Gratton et al. |
| 6,556,852 | B1 | 4/2003 | Schulze et al. |
| 6,697,656 | B1 | 2/2004 | Al-Ali |
| 6,930,608 | B2 | 8/2005 | Grajales et al. |
| 6,934,570 | B2 | 8/2005 | Kiani et al. |
| 7,010,337 | B2 * | 3/2006 | Furnary et al. ............... 600/325 |
| 7,029,467 | B2 | 4/2006 | Currier et al. |
| 7,197,357 | B2 | 3/2007 | Istvan et al. |
| 7,254,500 | B2 | 8/2007 | Makeig et al. |
| 7,377,794 | B2 | 5/2008 | Al-Ali et al. |
| 8,100,834 | B2 * | 1/2012 | Shuler .......................... 600/504 |
| 2001/0051767 | A1 | 12/2001 | Williams et al. |
| 2003/0225323 | A1 | 12/2003 | Kiani et al. |
| 2005/0148832 | A1 | 7/2005 | Reghabi et al. |
| 2005/0165323 | A1 | 7/2005 | Montgomery et al. |
| 2005/0251405 | A1 | 11/2005 | Kreiner et al. |
| 2005/0277819 | A1 | 12/2005 | Kiani et al. |

(Continued)

FOREIGN PATENT DOCUMENTS

CN 2691489 Y 4/2005
DE 3516338 11/1986

(Continued)

OTHER PUBLICATIONS

"Smaller Product, Tighter Tolerances Pose Dispensing Challenges for Medical Device Manufacturer," *Adhesives Age*, pp. 40-41 (Oct. 1997).

(Continued)

*Primary Examiner* — Eric Winakur
(74) *Attorney, Agent, or Firm* — Fletcher Yoder PC (57) ABSTRACT

A multisystem sensor is disclosed that includes a first sensor subsystem and a second sensor subsystem. The multisystem sensor includes a sensor body having both sensor subsystems. The first sensor subsystem may monitor a first physiological characteristic and the second sensor subsystem may monitor a second physiological characteristic. The sensor body may include an isolating portion configured to isolate the first sensor subsystem and the second sensor subsystem. The sensor body and/or isolating portion may include refractive components and/or filters to prevent interference between sensor subsystems.

23 Claims, 9 Drawing Sheets

(56) References Cited

U.S. PATENT DOCUMENTS

| | | |
|---|---|---|
| 2006/0122520 A1 | 6/2006 | Banet et al. |
| 2006/0211922 A1 | 9/2006 | Al-Ali et al. |
| 2006/0211923 A1 | 9/2006 | Al-Ali et al. |
| 2006/0211924 A1 | 9/2006 | Dalke et al. |
| 2006/0229509 A1 | 10/2006 | Al-Ali et al. |
| 2006/0241363 A1 | 10/2006 | Al-Ali et al. |
| 2006/0241708 A1 | 10/2006 | Boute |
| 2006/0258923 A1 | 11/2006 | Al-Ali et al. |
| 2006/0258924 A1 | 11/2006 | Al-Ali et al. |
| 2006/0258925 A1 | 11/2006 | Al-Ali et al. |
| 2006/0270920 A1 | 11/2006 | Al-Ali et al. |
| 2006/0281983 A1 | 12/2006 | Al-Ali et al. |
| 2007/0078311 A1 | 4/2007 | Al-Ali et al. |
| 2007/0149864 A1 | 6/2007 | Laakkonen |
| 2007/0149865 A1 | 6/2007 | Laakkonen |
| 2007/0208262 A1 | 9/2007 | Kovacs |
| 2007/0260132 A1 | 11/2007 | Sterling |
| 2008/0097910 A1 | 4/2008 | Dicks et al. |
| 2008/0097914 A1 | 4/2008 | Dicks et al. |
| 2008/0220633 A1 | 9/2008 | Al-Ali et al. |
| 2008/0221413 A1 | 9/2008 | Hoarau |
| 2008/0242958 A1 | 10/2008 | Al-Ali et al. |
| 2008/0300474 A1 | 12/2008 | Benni et al. |

FOREIGN PATENT DOCUMENTS

| | | |
|---|---|---|
| DE | 3703458 | 8/1988 |
| DE | 19632361 | 2/1997 |
| EP | 0127947 | 12/1984 |
| EP | 0204259 | 12/1986 |
| EP | 0531631 | 3/1993 |
| FR | 2685865 | 7/1993 |
| JP | 6014906 | 1/1994 |
| WO | WO9502358 | 1/1995 |
| WO | WO9736536 | 10/1997 |

OTHER PUBLICATIONS

Crilly, Paul B., et al.; "An Integrated Pulse Oximeter System for Telemedicine Applications," *IEEE Instrumentation and Measurement Technology Conference*, Ottawa, Canada; May 19-21, 1997; pp. 102-104.

DeKock, Marc; "Pulse Oximetry Probe Adhesive Disks: a Potential for Infant Aspiration," *Anesthesiology*, vol. 89, pp. 1603-1604 (1998).

Rhee, Sokwoo, et al.; "The Ring Sensor: a New Ambulatory Wearable Sensor for Twenty-Four Hour Patient Monitoring," *Proceedings of the 20th annual International Conference of the IEEE Engineering in Medicine and Biology Society*, 1998, vol. 20, No. 4, pp. 1906-1919.

Yang, Boo-Ho, et al.; "A Twenty-Four Hour Tele-Nursing System Using a Ring Sensor," *Proceedings of the 1998 IEEE International Conference on Robotics & Automation*, Leaven, Belgium, May 1998; pp. 387-392.

Lutter, N., et al.; "Comparison of Different Evaluation Methods for a Multi-wavelength Pulse Oximeter," *Biomedizinische Technik*, vol. 43, (1998).

Yang, Boo-Ho, et al.; "Development of the ring sensor for healthcare automation," *Robotics and Autonomous Systems*, vol. 30, pp. 273-281 (2000).

Rhee, Sokwoo, et al.; "Artifact-Resistant, Power-Efficient Design of Finger-Ring Plethysmographic Sensor—Part I: Design and Analysis," *Proceedings of the 22nd Annual EMBS International Conference*, Chicago, Illinois; Jul. 23-28, 2000; pp. 2792-2795.

Rhee, Sokwoo, et al.; "Artifact-Resistant, Power-Efficient Design of Finger-Ring Plethysmographic Sensor—Part II: Prototyping and Benchmarking," *Proceedings of the 22nd Annual EMBS International Conference*, Chicago, Illinois; Jul. 23-28, 2000; pp. 2796.

Schulz, Christian Eric; "Design of a Pulse Oximetry Sensor Housing Assembly," California State University Master's Thesis, *UMI Dissertation Services*, UMI No. 1401306, (May 2000) 63 pages.

Yokota, Nakaura, Takahashi, et al.; "Pilot Model of a Reflectance-Type Pulse Oximeter for Pre-hospital Evaluation," *Journal of the Japanese Society of Emergency Medicine*, Kanto Region, vol. 21, pp. 26-27 (2000) (Article in Japanese—contains English summary.

Gisiger, P.A., et al.; "OxiCarbo®, a single sensor for the non-invasive measurement of arterial oxygen saturation and $CO_2$ partial pressure at the ear lobe," *Sensor and Actuators*, vol. B-76, pp. 527-530 (2001).

Rhee, Sokwoo, et al.; "Artifact-Resistant, Power-Efficient Design of Finger-Ring Plethysmographic Sensor," *IEEE Transactions on Biomedical Engineering*, vol. 48, No. 7, pp. 795-805 (Jul. 2001).

Maletras, Francois-Xavier, et al.; "Construction and calibration of a new design of Fiber Optic Respiratory Plethysmograph (FORP)," *Optomechanical Design and Engineering, Proceedings of SPIE*, vol. 4444, pp. 285-293 (2001).

Earthrowl-Gould, T., et al.; "Chest and abdominal surface motion measurement for continuous monitoring of respiratory function," *Proc. Instn Mech Engrs*, V215, Part H; pp. 515-520 (2001).

Irie, A., et al.; "Respiration Monitors—Pulse Oximeters," *Neonatal Care*, vol. 15, No. 12, pp. 78-83 (2002) (Article in Japanese—contains English summary of article).

Warren, Steve, et al.; "Wearable Sensors and Component-Based Design for Home Health Care," *Proceedings of the Second Joint EMBS/BMES Conference*, Houston, Texas; Oct. 23-26, 2002; pp. 1871-1872.

Yoon, Gilwon, et al.; Multiple diagnosis based on Photo-plethysmography: hematocrit, SpO2, pulse and respiration, *Optics in Health Care and Biomedical optics: Diagnostics and Treatment; Proceedings of the SPIE*, vol. 4916; pp. 185-188 (2002).

Matsui, A., et al.; "Pulse Oximeter," *Neonatal Care*, vol. 16, No. 3, pp. 38-45 (2003) (Article in Japanese—contains English summary of article).

Nakagawa, M., et al.; "Oxygen Saturation Monitor," *Neonatal Monitoring*, vol. 26, No. 5, pp. 536-539 (2003) (Article in Japanese—contains English summary of article).

\* cited by examiner

MULTIPLE SENSOR ASSEMBLIES AND CABLES IN A SINGLE SENSOR BODY

BACKGROUND

The present disclosure relates generally to medical devices and, more particularly, to medical sensors for monitoring physiological characteristics.

This section is intended to introduce the reader to aspects of the art that may be related to various aspects of the present disclosure, which are described and/or claimed below. This discussion is believed to be helpful in providing the reader with background information to facilitate a better understanding of the various aspects of the present disclosure. Accordingly, it should be understood that these statements are to be read in this light, and not as admissions of prior art.

In the field of medicine, doctors often desire to monitor certain physiological characteristics of their patients. To allow such monitoring, various types of sensors and monitors may be employed by caregivers. For example, to measure certain characteristics, optical based sensors may be utilized that transmit electromagnetic radiation, such as light, through a patient's tissue and then photo-electrically detect the absorption and scattering of the transmitted or reflected light in such tissue. The physiological characteristics of interest may then be calculated based upon the amount of light absorbed and/or scattered or based upon changes in the amount of light absorbed and/or scattered. In such measurement approaches, the light passed through the tissue is typically selected to be of one or more wavelengths that may be absorbed and/or scattered by one or more constituents of the blood or tissue in an amount correlative to the amount of the constituents present in the blood or tissue.

Other types of sensors may also be used to measure various physiological characteristics of a patient. For example, certain types of sensors (such as electrocardiogram (ECG) or electroencephalogram (EEG) leads) may measure electrical potentials or properties that can yield physiological information. Other types of sensors may measure internal or external temperature of a patient or may detect acoustic or sound data that can be related to physiological characteristics of a patient. Such temperature or acoustic data may in turn be used to derive data about a physiological characteristic of the patient.

The various types of patient sensors may communicate with respective monitoring equipment or devices. For example, a patient monitor, such as a pulse oximeter, may receive data from a corresponding sensor and determine a corresponding physiological characteristic. However, monitoring of multiple physiological characteristic requires use of multiple sensors, monitors, diagnostic tools, etc. For example, monitoring of each physiological characteristic of interest may use a different sensor, different cables, different monitors, etc. Typically, each sensor may only be capable of monitoring one physiological characteristic at a time. Further, any configurability may be limited, as the hardware in the sensor may be selected and configured to monitoring one physiological characteristic.

BRIEF DESCRIPTION OF THE DRAWINGS

Advantages of the disclosure may become apparent upon reading the following detailed description and upon reference to the drawings in which.

DETAILED DESCRIPTION OF SPECIFIC EMBODIMENTS

The present disclosure is generally directed to the use of a sensor body supporting or including multiple types of sensing devices. As discussed herein, each type of sensing device on the sensor may be configured to communicate with the same monitor or may communicate with different respective monitors, such as via separate physical cables or by wireless signals. In this manner, the number of sensor bodies affixed to a patient may be limited while still allowing different types of sensor data to be collected for the patient.

Figure 1:
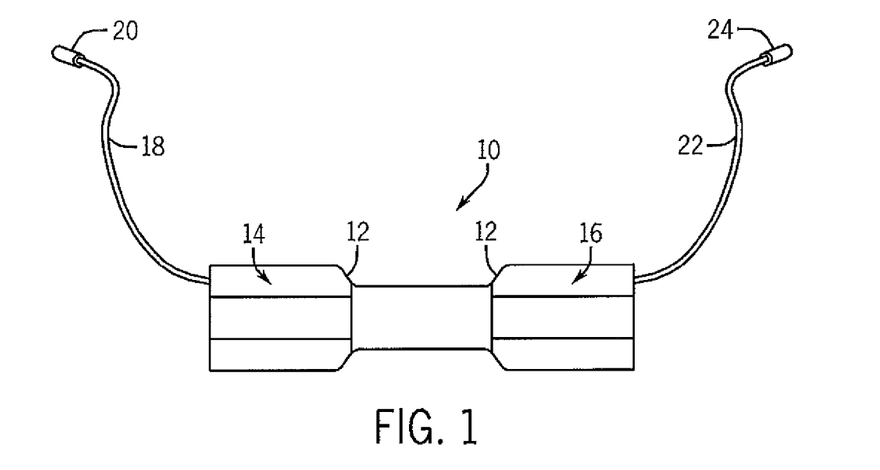
FIG. 1 depicts a multisystem sensor in accordance with an embodiment of the present disclosure.

With the foregoing in mind, FIG. 1 depicts a multisystem sensor 10 having a sensor body 12 in accordance with an embodiment of the present disclosure. The multisystem sensor 10 includes a first sensor subsystem 14 and a second sensor subsystem 16. Each sensor subsystem 14 and 16 includes components used to measure one or more respective physiological characteristics of a patient to which the sensor 10 is applied. In one embodiment the first sensor subsystem 14 may include some or all of the same components as the second sensor subsystem 16. In other embodiments, each sensor subsystem 14 and 16 may include different components.

As shown in FIG. 1, the sensor 10 may be a bandage-type sensor having a generally flexible sensor body 12 to enable conformable application of the sensor 10 to a sensor site on a patient, such as via adhesion. The sensor 10 may be secured to a patient via adhesive on the underside of the sensor body 12 or by an external device such as headband or other elastic tension device.

In one embodiment, each sensor subsystem 14 and 16 may communicate via a separate cable and connector. The first sensor subsystem 14 may include a cable 18 having a connector 20 extending from the sensor subsystem 14 to provide for connection of the sensor 10 to a monitor. The cable 18 may be communicatively coupled to an emitter 26 (FIG. 2), a detector 28 (FIG. 2), and any other components of the first sensor subsystem 14 to carry signals to and from the sensor subsystem 14. For example, the cable 18 may communicate drive signals from a monitor to the first sensor subsystem 14 and may communicate signal output from the first sensor subsystem 14 to the monitor. Similarly, the second sensor subsystem 16 may include a separate cable 22 having a connector 24 extending from the second sensor subsystem 16 to connect the sensor 10 to a monitor.

The connectors 20 and 24 may be similar or different. In some embodiments, each sensor subsystem 14 and 16 may be connected to a separate respective monitor by the cables 18 and 22. In some embodiments, the cables 18 and 22, and/or the connectors 20 and 24, may be color-coded to differentiate the connections to each sensor subsystem 14 and 16, so that each sensor subsystem 14 and 16 may be connected to an appropriate monitor or connector. In other embodiments, each sensor subsystem 14 and 16 may be connected to a single monitor such that each connector couples to the same monitor. In other embodiments, the sensor 10 may include different cable configurations, or wireless configurations, as discussed further below.

It should be understood that the sensor 10 may be configured to hold a variety of different sensor types used to monitor and/or measure the same or different physiological characteristics. In some embodiments, the first sensor subsystem 14 and/or the second sensor subsystem 16 may include optical sensor systems for optical interrogation of blood and tissue constituents. In other embodiments, the first sensor subsystem 14 and/or the second sensor subsystem 16 may include other types of sensor components, such as components not directed to the optical interrogation of the patient tissues. For example, the first sensor subsystem 14 and/or the second sensor subsystem 16 may include an acoustic transducer or microphone, an electrode for measuring electrical activity or potentials (such as for electrocardiography), pressure sensors, motion sensors, temperature sensors, etc. Further, more than two sensor subsystems of the same or different types may be provided on a given sensor and, as discussed in greater detail below, the different sensor subsystems may communicate to the same or different monitors and/or over the same or different physical cables or wireless links.

Figure 2:
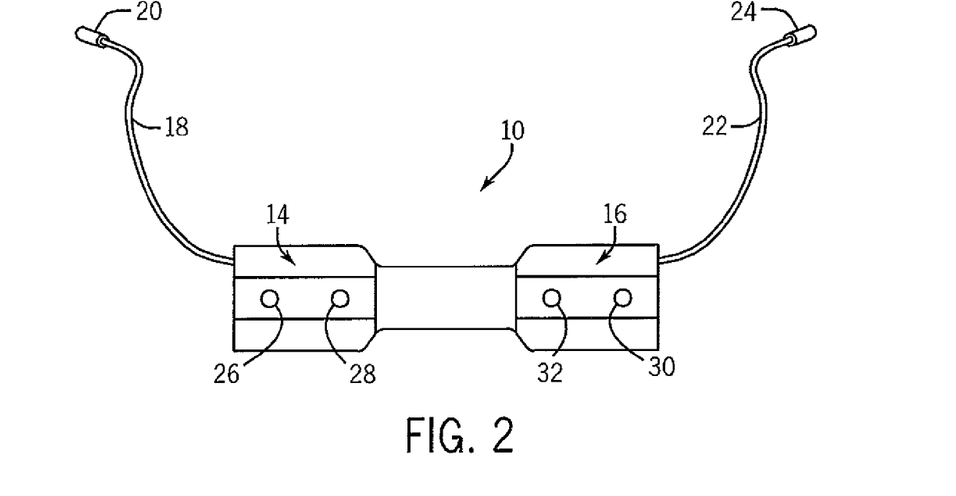
FIG. 2 depicts the multisystem sensor of FIG. 1 having optical sensor subsystems in accordance with an embodiment of the present disclosure.

FIG. 2 depicts the multi-system sensor 10 having optical sensor subsystems in accordance with an embodiment of the present disclosure. In the depicted embodiment, the first sensor subsystem 14 may include an optical sensor system having an emitter 26 and a detector 28. In one embodiment, the second sensor subsystem 16 may also include a second optical sensor system having an emitter 30 and a detector 32.

Together, the emitter 26 and the detector 28 of the first sensor subsystem 14 may be used to determine a first physiological characteristic of a patient. For example, the emitter 26 may emit light at one, two, three, or more wavelengths for emission into a sensor site on a patient. The detector 28 of the first sensor subsystem 14 may include photo-detectors for detecting the wavelengths of light emitted from the emitter 26 and converting the intensity of the received light into an electrical signal. The light intensity is directly related to the absorbance and/or reflectance of light in the blood and/or tissue of a patient. The first sensor subsystem 14 may be configured to measure any suitable physiological characteristic, either alone or in combination with other data, such as from a second sensor. Such suitable physiological characteristic may include, but are not limited to, blood and/or tissue oxygenation and perfusion, respiratory rate, respiratory, effort, continuous non-invasive blood pressure, cardiovascular effort, glucose levels, level of consciousness, hematocrit (or equivalently, total hemoglobin concentration), dysfunctional hemoglobin content, and/or hydration. The emitter 26 and detector 28 may be communicatively coupled to the cable 18 and the connector 20. Drive signals may be provided to the emitter 26 over the connector 20 and cable 18, and output signals generated by the detector 28 may be provided to a monitor over the connector 20 and cable 18.

Similarly, the emitter 30 and detector 32 of the second sensor subsystem 16 may be used to determine a second physiological characteristic of a patient. The physiological characteristic determined by the second sensor subsystem 16 may be different than or the same as the physiological characteristic determined by the first sensor subsystem 14. As with the first sensor subsystem 14, the emitter 30 of the second sensor subsystem 16 may also emit one, two, three, or more wavelengths for emission into a sensor site of the patient. Likewise, the detector 32 of the second sensor subsystem 16 may include photo-detectors for detecting the wavelengths of light emitted from the emitter 30 and converting the intensity of the received light into an electrical signal. As discussed with respect to the first sensor subsystem 14, the light intensity is directly related to light from emitter 30 that is absorbed and/or reflected in the blood and/or tissue of a patient so that a suitable physiological characteristic may be measured. For example, the second sensor subsystem 16 may be configured to detect any suitable physiological characteristic, such as those physiological characteristics listed with respect to the first sensor subsystem 14. The emitter 30 and detector 32 may be communicatively coupled to the cable 22 and the connector 24. Drive signals may be provided to the emitter 30 over the connector 24 and cable 22, and output signals generated by the detector 32 may be provided to a monitor over the connector 24 and cable 22.

In one embodiment, the sensor 10 may operate as a reflectance-type sensor, such that the emitter 26 and detector 28 of the first sensor subsystem 14 are on the same side of the tissue at the sensor site and/or the emitter 30 and detector 32 of the second sensor subsystem 16 are on the same side of the tissue at the sensor site such that reflected light is measured. In other embodiments, the sensor 10 may be configured and applied as a transmittance-type sensor in which the emitter and detector of a sensor subsystem are placed on opposite sides of tissue bed at a sensor placement site such that light transmitted through the tissue is measured. In yet other embodiments, the sensor 10 may be applied as a combination reflectance- and transmittance-type sensor. For example, the first sensor subsystem 14 may be applied such that the emitter 26 and detector 28 are arranged in a transmittance-type configuration and the second sensor site 16 may be applied such that the emitter 30 and detector 32 are arranged in a reflectance-type configuration.

Figure 3:
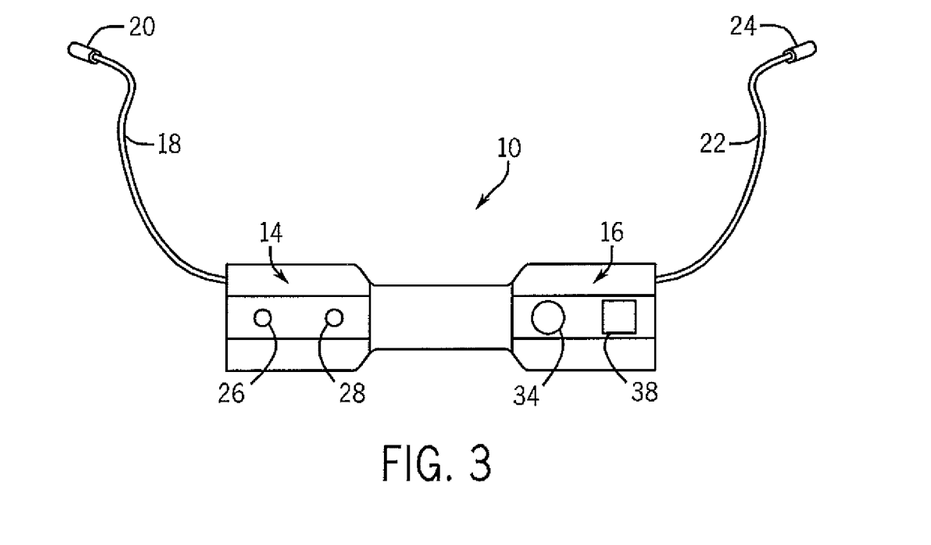
FIG. 3 depicts the multisystem sensor of FIG. 1 having an optical sensor subsystem and another sensor subsystem in accordance with an embodiment of the present disclosure.

FIG. 3 depicts the multi-system sensor 10 having an optical sensor subsystem and another sensor subsystem modality in accordance with an embodiment of the present disclosure. In the depicted embodiment, the first sensor subsystem 14 may include an optical sensor system having the emitter 26 and the detector 28. The second sensor subsystem 16 may include an acoustic microphone or transducer 34 and/or a temperature sensor 38. The temperature sensor 38 may measure internal or external temperature of the tissue of a patient at the sensor site. The acoustic microphone or transducer 34 of the second sensor subsystem 16 may detect acoustic or sound data that can be related to physiological characteristics of the patient. As discussed above, the emitter 26 and the detector 28 may be communicatively coupled to the cable 18 and the connector 20 to couple the first sensor subsystem 12. The acoustic transducer 34 and/or the temperature sensor 38 may be communicatively coupled to the cable 22 and the connector 24 to connect each component to a monitor. The acoustic transducer 34 and/or temperature sensor 38 may receive power and/or control signals from a monitor and may output signals to a monitor via the cable 22 and the connector 24.

Figure 4:
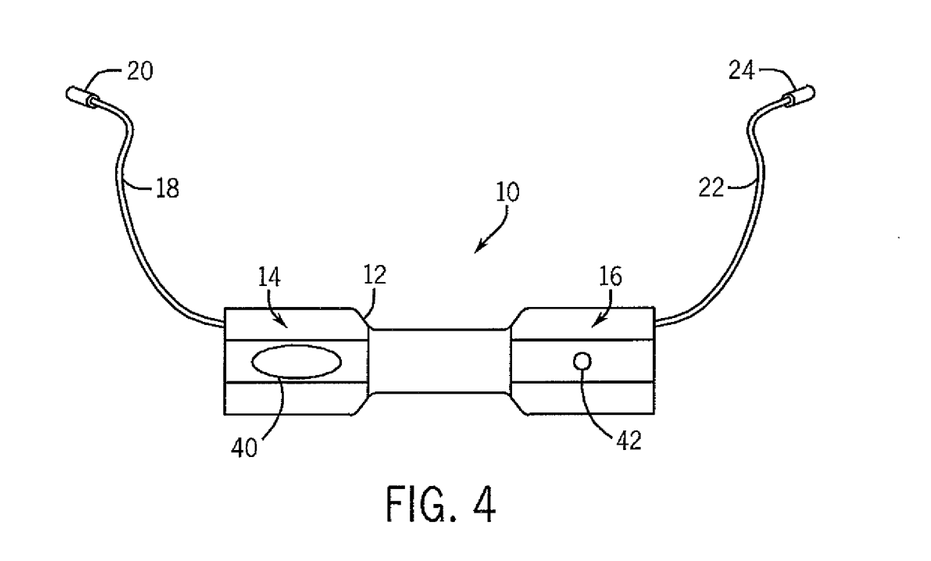
FIG. 4 depicts the multisystem sensor of FIG. 1 having a mechanical pressure sensor subsystem and an electrical sensor subsystem in accordance with an embodiment of the present disclosure.

FIG. 4 depicts the multi-system sensor 10 having a mechanical pressure sensor subsystem and an electrical sensor subsystem in accordance with an embodiment of the present disclosure. In the depicted embodiment, the first sensor subsystem 14 may include a pressure sensor subsystem having a pressure sensor 40, such as a mechanical or piezoelectric strain gauge sensor. The pressure sensor 40 may provide a signal indicative of the attachment pressure at the measurement site to enable monitoring of the attachment or the multi-system sensor and/or the desired pressure at the sensor site. The pressure sensor 40 may be communicatively coupled to the cable 18 and connector 20 to enable monitoring of the pressure sensor 40 by a monitor or gauge.

The second sensor subsystem 16 may include an electrical sensor 42, such as an electrical probe, lead, contact, or other suitable sensor apparatus. The electrical sensor 42 may include, for example, electrocardiogram (ECG) or electroencephalogram (EEG) leads, and may be used to monitor electrical potentials, impedances or other properties that may be used to measure or monitor a physiological characteristic of interest. In such an embodiment, the electrical sensor 42 may be used in conjunction with one or more other electrical sensor located at the same or different sensor sites. The electrical sensor 42 may be communicatively coupled to the cable 22 and the connector 24. The electrical sensor 42 may receive power or signals from a monitor and may send output to the monitor via the cable 22 and connector 24.

Figure 5:
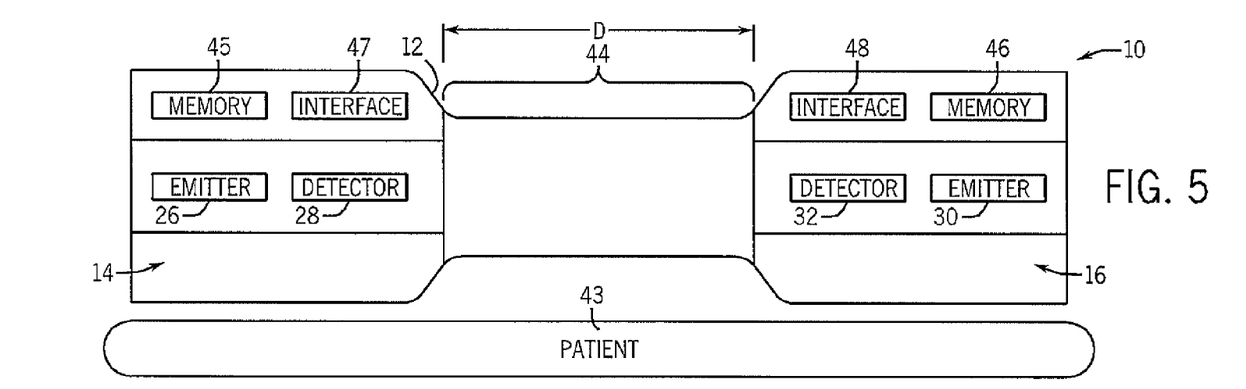
FIG. 5 is a block diagram of the multisystem sensor of FIG. 2 in accordance with an embodiment of the present disclosure.

FIG. 5 is a block diagram of the sensor 10 and the sensor subsystems 14 and 16 of FIG. 2 in accordance with an embodiment of the present disclosure in which the sensor subsystems are optical sensor subsystems. As noted above, in the depicted embodiment the first sensor subsystem 14 includes the emitter 26 and the detector 28 configured to monitor a first physiological characteristic at a first sensor site of a patient 43 while the second sensor subsystem 16 includes the emitter 30 and the detector 32 configured to monitor a second physiological characteristic at a second sensor site of the patient 43. Though the first and second sensor subsystems 14 and 16 are described below in FIGS. 5-7 in the context of optical sensing arrangements (e.g., the emission and detection of light energy at certain wavelengths), such examples are merely provided to facilitate explanation.

In one embodiment, the sensor body 12 of the sensor 10 may include an isolating portion 44 between the first sensor subsystem 14 and the second sensor subsystem 16. The isolating portion 44 may include any suitable material and/or components to optically, acoustically, and/or electrically isolate the sensor subsystems 14 and 16 from each other. The isolating portion 44 may include a portion of the sensor body 12 having a thickness or separation distance D. The distance D may be selected to provide sufficient distance between the first sensor subsystem 14 and the second sensor subsystem 16 such that light (or other energy) emitted from the first sensor subsystem 14 is attenuated before it reaches the detector of the second sensor subsystem 16 and vice-versa.

In some embodiments, one or both of the first sensor subsystem 14 and the second sensor subsystem 16 may include a memory and/or encoder 45, 46 for storing information relating to the respective sensor subsystem and/or sensor 10, such as sensor type, calibration information (e.g., calibration coefficients), etc. In some embodiments, the sensor 10 may include a single memory storing information related to the sensor 10, the first sensor subsystem 14, and the second sensor subsystem 16.

The sensor 10 may also include wireless communication capability. In one embodiment, the first sensor subsystem 14 may include a wireless interface 47 for communication between the first sensor subsystem 14 and a monitor or other wireless device. The wireless interface 47 may provide for RF communication over any suitable wireless network protocol. Additionally, or alternatively, the second sensor subsystem 16 may include a wireless interface 48 for communication between the second sensor subsystem 16 and a monitor or other wireless device.

Figure 6:
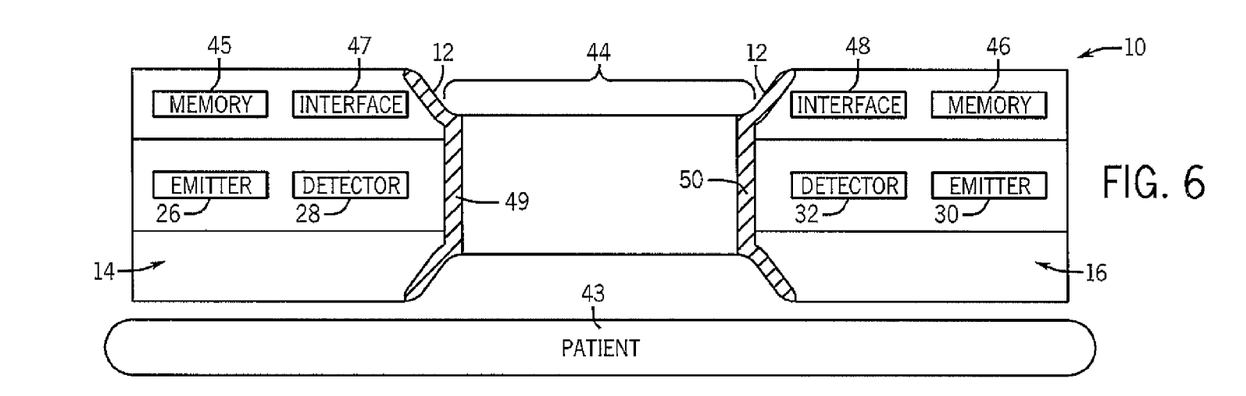
FIG. 6 is a block diagram of the multisystem sensor of FIG. 2 having reflective components in accordance with an embodiment of the present disclosure.

In other embodiments, the sensor body 12 and isolating portion 44 may include various components to isolate or provide additional isolation between the first sensor subsystem 14 and the second sensor subsystem 16. FIG. 6 is a block diagram of the sensor 10 and the sensor subsystems 14 and 16 of FIG. 2 having reflective components in accordance with an embodiment of the present disclosure. In the depicted embodiment, the sensor body 12 may include one or more reflective components (e.g., mirrors, lenses, etc.) disposed between the first sensor subsystem 14 and the second sensor system 16 to prevent transmission of light through the sensor body 12 itself. A first refractive component 49 may be disposed around the first sensor subsystem 14 to prevent scattering of light emitted from the emitter 26 from reaching the detector 32 of the second sensor subsystem 16. The refractive component 49 may be disposed between the emitter 26 and the detector 28, or between the sensor subsystem 14 and the isolating portion 44 The refractive index of the reflective component 49 may be selected to ensure that some or substantially all of the light emitted from the emitter 26 of the first sensor subsystem 14 is received by the detector 28. Additionally, or alternatively, a second refractive component 50 may be disposed in or around the second sensor subsystem 16 to prevent scattering of light from the emitter 30 from reaching the detector 28 of the first sensor subsystem 14. The refractive component 50 may be disposed between the emitter 30 and the detector 32, or between the sensor subsystem 16 and the isolating portion 44. Thus, the refractive index of the second refractive component 50 may be selected to ensure that some or substantially all of the light emitted from the emitter 30 of the second sensor subsystem 16 is received by the detector 32. The reflective components 49 and/or 50 may be disposed in any suitable portion of the sensor body 12, such as in the isolating portion 44 or in each respective sensor subsystem 14 and 16.

Figure 7:
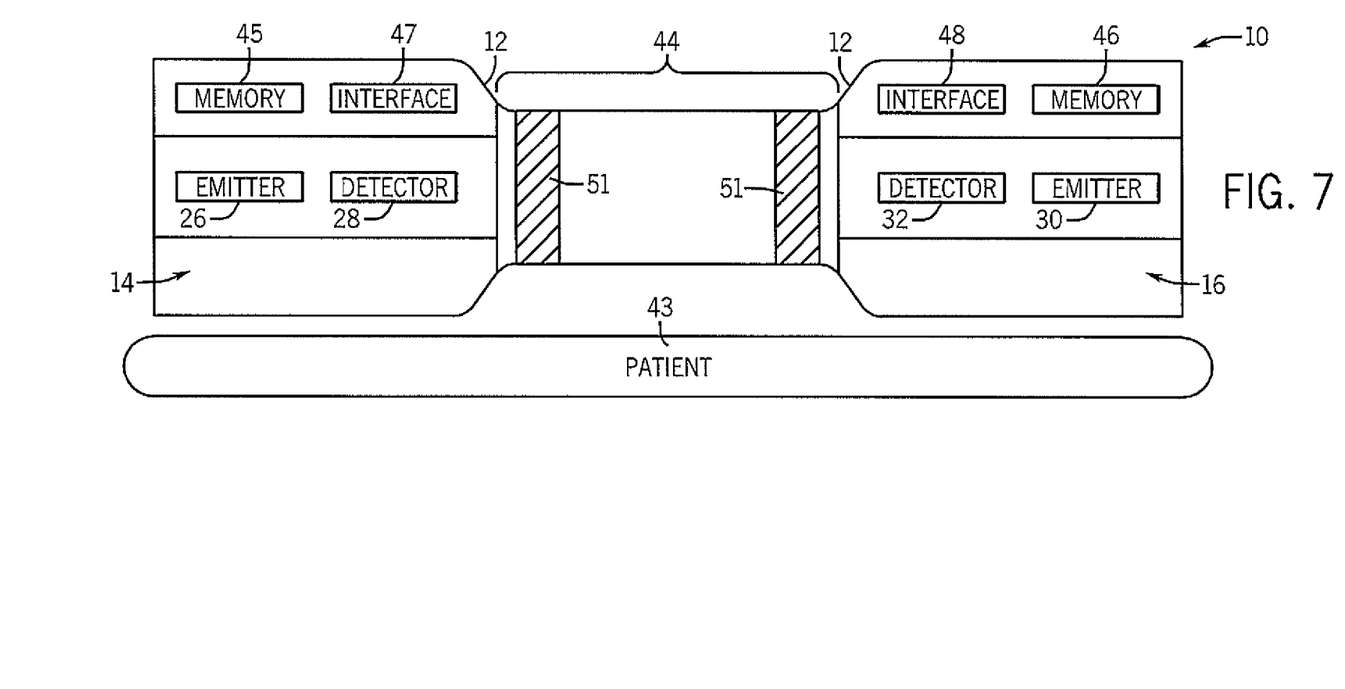
FIG. 7 is a block diagram of the multisystem sensor of FIG. 2 having filters in accordance with an embodiment of the present disclosure.

FIG. 7 is a block diagram of the sensor 10 and the sensor subsystems 14 and 16 of FIG. 2 having filters disposed between sensor subsystems 14 and 16 in accordance with an embodiment of the present disclosure. In the depicted embodiment, one or more filters 51 may be disposed between the first sensor subsystem 14 and the second sensor subsystem 16, such as in the isolating portion 44. The filters 51 may be selected to reject wavelengths of light not needed by a particular subsystem. For example, one of the filters 51 may be disposed to reject wavelengths of light emitted from the emitter 26 of the first sensor subsystem 14, preventing light of this wavelength from reaching the second sensor subsystem 16. In another example, one of the filters 51 may be disposed to reject wavelengths of light emitted from the emitter 30 of the second sensor subsystem 16, preventing light of this wavelength from reaching the first sensor subsystem 14.

Figure 8:
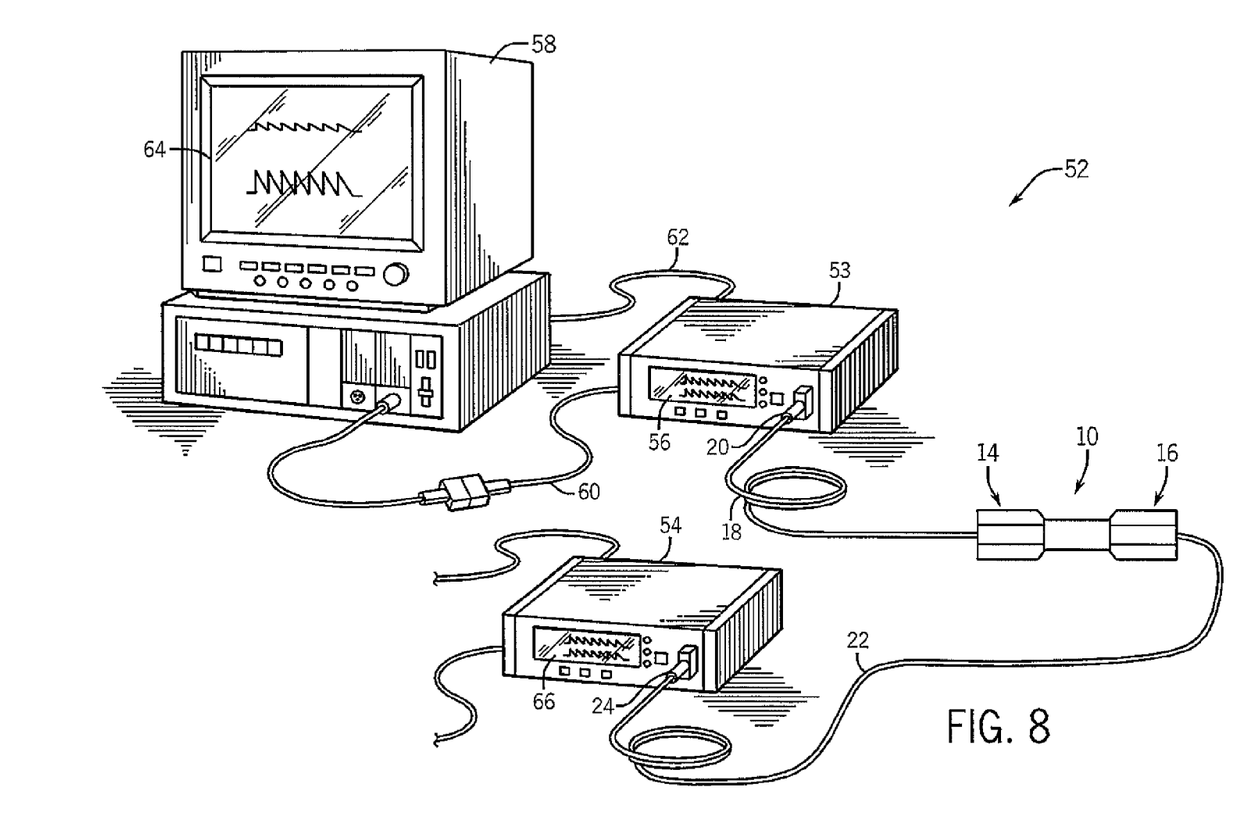
FIG. 8 depicts a medical monitoring system having the multisystem sensor of FIG. 1 in accordance with an embodiment of the present disclosure.

With the foregoing different implementations of a multisystem sensor 10 in mind, FIG. 8 depicts a medical monitoring system 52 having the multisystem sensor 10 in accordance with an embodiment of the present disclosure. The medical monitoring system 52 enables monitoring of two physiological characteristics using the single sensor 10. For example, a first sensor subsystem 14 of the sensor 10 may be coupled to a first monitor 53 via the cable 18 and connector 20 and a second sensor subsystem 16 of the sensor 10 may be separately coupled to a second monitor 54 via the cable 22 and connector 24. The monitors 53 and 54 may be configured to calculate one, two, three, or more physiological characteristics of a patient from signals received from the sensor 10.

The sensor 10 may be applied to a patient to monitor a first physiological characteristic via the first sensor subsystem 14 and a second physiological characteristic via the second sensor subsystem 16. For example, the monitors 53, 54 may be configured to provide signals to the respective connected sensor subsystems to drive the emitters and to receive signals generated by the detectors. The monitors 53, 54 may include respective displays 56, 66 configured to display information regarding the respective physiological characteristics, information about the systems, and/or alarm indications. In some embodiments, the monitors 53, 54 may be configured to determine any suitable physiological characteristic from the sensor 10, such as blood and/or tissue oxygenation and perfusion, respiratory rate, respiratory effort, continuous non-invasive blood pressure, cardiovascular effort, glucose levels, level of consciousness, hematocrit, dysfunctional hemoglobin content, and/or hydration.

Furthermore, to upgrade conventional operation provided by a monitor and to provide additional functions, a monitor, such as the monitor 53, may be coupled to a multi-parameter patient monitor 58 via a cable 60 connected to a sensor input port or via a cable 62 connected to a digital communication port. In addition to the monitor 53, or alternatively, the multi-parameter patient monitor 58 may be configured to calculate physiological characteristics and to provide a central display 64 for information from the monitor 53 and from other medical monitoring devices or systems. In addition, the monitor 53 and/or the multi-parameter patient monitor 58 may be connected to a network to enable the sharing of information with servers or other workstations.

Figure 9:
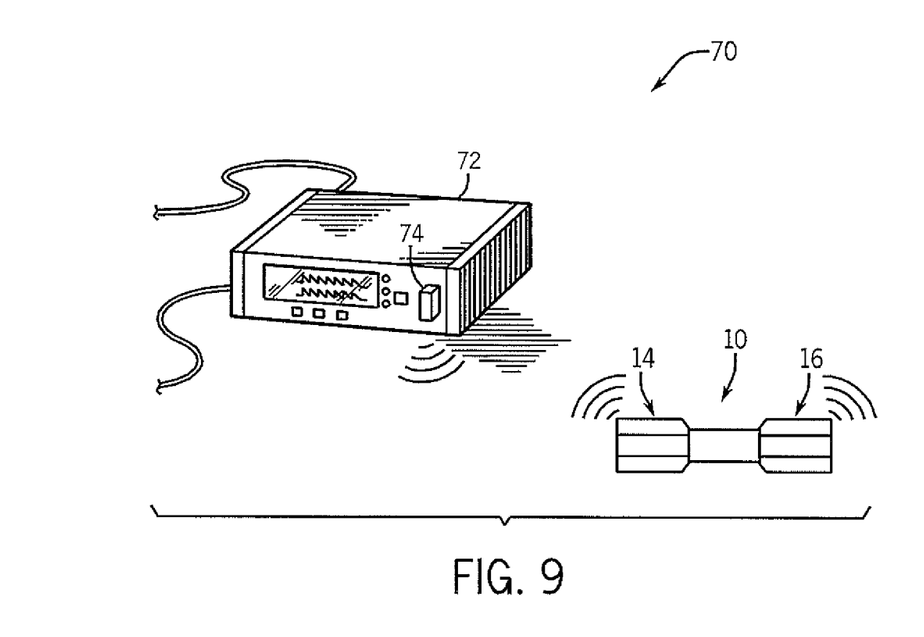
FIG. 9 depicts a wireless medical monitoring system having the multisystem sensor of FIG. 1 in accordance with an embodiment of the present disclosure.

FIG. 9 depicts a wireless medical monitoring system 70 having the sensor 10 in wireless communication with a monitor 72 in accordance with another embodiment of the present disclosure. In the wireless system 70, embodiments of the sensor 10 may include one or more batteries to provide power to the sensory subsystems 14 and 16, and/or the wireless interfaces 47 and 48.

The monitor 72 may include one or more wireless interfaces configured to communicate with one or more sensors 10 and to wirelessly monitor one or more physiological characteristics. For example, the monitor 72 may be configured to determine multiple physiological characteristics from sensor data wirelessly received from one or more sensors subsystems, including different sensor subsystems disposed on a single sensor 10. Thus, the monitor 72 may wirelessly communicate with the first sensor subsystem 14 and/or the second sensor subsystem 16 of the sensor 10. Additionally, the monitor 72 may include a connector 74 to provide for a wired connection to a sensor (such as the first sensor subsystem 14 or the second sensor subsystem 16) if such a wired connection is desired.

In one embodiment, the monitor 72 may determine a first physiological characteristic of patient based on data wirelessly received from the first sensor subsystem 14 and/or may determine a second physiological characteristic based on data received from the second sensor subsystem 16. The monitor 72 may also provide signals to the first sensor subsystem 14 and/or to the second sensor subsystem 16 to facilitate operation of the sensor subsystems. It should be appreciated that each sensor subsystem 14 and 16 and/or any other provided sensor subsystems may communicate on a different wireless channel and/or frequency to avoid interference. In some embodiments, any combination of wireless and wired communication may be used. For example, the first sensor subsystem 14 may be wirelessly coupled to the monitor 72 and the second sensor subsystem 16 may be physically coupled to the monitor 72 via the cable 22 and connector 24.

Figure 10:
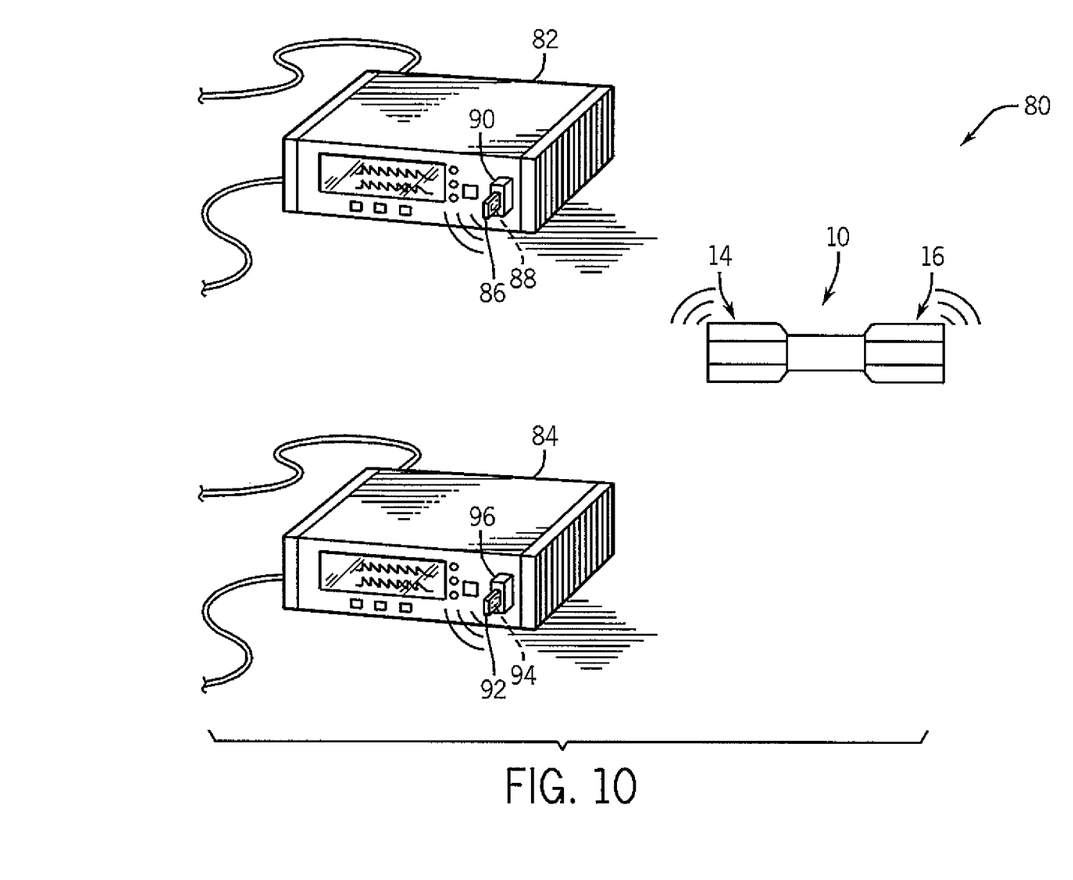
FIG. 10 depicts a wireless medical monitoring system having the multisystem sensor in wireless communication with multiple monitors in accordance with an embodiment of the present disclosure.

FIG. 10 depicts a medical monitoring system 80 having the multisystem sensor 10 in wireless communication with multiple monitors in accordance with another embodiment of the present disclosure. As noted above, the sensor 10 may include the first sensor subsystem 14 having a first wireless interface 47 and the second sensor subsystem 16 having a second wireless interface 48. Thus, each sensor subsystem 14 and 16 may be capable of independent wireless communication with the same or different monitors via the respective wireless interfaces 47 and 48. Thus, the first sensor subsystem 14 may wirelessly communicate with a first monitor 82 and the second sensor subsystem 16 may wirelessly communicate with a second monitor 84. As also noted above, in a wireless configuration, embodiments of the multisystem sensor 10 may include one or more batteries to provide power to components of each sensor subsystem 14 and 16.

To facilitate wireless communication with the sensor 10, the medical monitoring system 80 may include a dongle 86 having a wireless interface 88 configured to communicate with a sensor subsystem, thereby allowing the exchange of signals between the monitor 82 and the sensor 10 when the dongle 86 is inserted into the monitor 82. As shown in FIG. 10, the dongle 86 may be plugged into a connector 90 at the monitor 82, providing the monitor with a physical connection to the dongle 86, thereby mimicking a physical connection to the sensor 10 in certain embodiments. The dongle 86 may wirelessly communicate with the wireless interface 47 of the first sensor subsystem 14 of the sensor 10. For example, in one embodiment, the dongle 86 may provide drive signals to the emitter 26 of the first sensor subsystem 14 and may receive signals generated by the detector 28 of the first sensor subsystem 14. The dongle 86 may communicate any received signals from the first sensor subsystem 14 to the monitor 82 over the connector 90. Thus, the dongle 86 may allow wireless communication with the multisystem sensor 10 even if the monitor is normally incapable of such wireless communication.

In some embodiments, the second monitor 84 may be capable of wireless communication with the second sensor subsystem 16, such as described above in FIG. 9. In other embodiments, a second dongle 92 having a wireless interface 94 may be plugged into a connector 96 of the second monitor 84, receiving and transmitting wireless signals between the second sensor subsystem 16 and the monitor 84. For example, the second dongle 84 may provide drive signals to an emitter 30 of the second sensor subsystem 16 and may receive signals generated by a detector 32 of the second sensor subsystem 16.

It should be appreciated that in such an embodiment, each dongle 86 and 92 and sensor subsystems 14 and 16 may communicate on different wireless channels and/or frequency to avoid interference. In other embodiments, any combination of wireless and wired communication may be used. For example, the first sensor subsystem 14 may be wirelessly coupled to the first monitor 82 via the dangle 86, and the second sensor subsystem 16 may be physically coupled to the second monitor 84 at the connector 96 via the cable 22 and the connector 24. In other embodiments, the first sensor subsystem 14 may be wirelessly coupled to the first monitor 82 via the dangle 86 and the second sensor subsystem 16 may be wirelessly coupled to the monitor 84 without the use of any dongles, such as via a wireless functionality built into the monitor 84.

Figure 11:
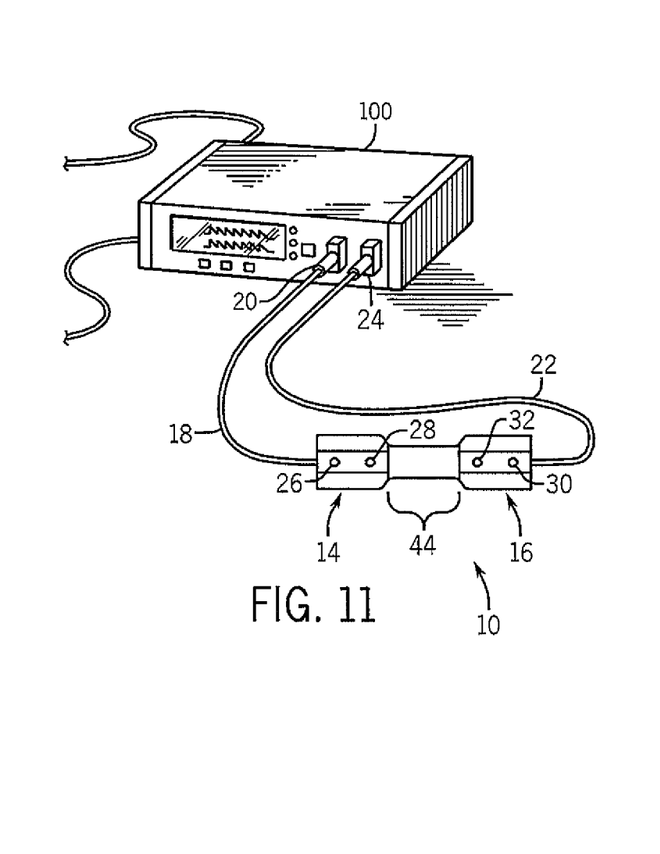
FIG. 11 depicts a multisystem sensor having two cables coupled to a single monitor in accordance with an embodiment of the present disclosure.

In other embodiments, a multisystem sensor 10 may be coupled to a single monitor by one cable or two cables. Though the sensors are described in FIGS. 11-13 below in the context of optical sensing arrangements (e.g., the emission and detection of light energy at certain wavelengths), such examples are merely provided to facilitate explanation. Other types of sensor subsystems may also be present and/or employed. FIG. 11 depicts an embodiment of the multisystem sensor 10 having the first cable 18 and connector 20 and the second cable 22 and connector 24 coupled to a single monitor 100. As described above, the multisystem sensor 10 may include a sensor body 12 having a first sensor subsystem 14 and a second sensor subsystem 16. In one embodiment, such as illustrated above in FIG. 2, the first sensor subsystem 14 may include the emitter 26 and the detector 28, and the second system subsystem 16 may include an emitter 30 and detector 32. As described above, the first sensor subsystem 14 may be configured to monitor a first physiological characteristic and generate a signal corresponding to the physiological characteristic. Similarly, the second sensor subsystem 16 may be configured to monitor a second physiological characteristic and generate a signal in response thereto. As discussed above in FIGS. 5-7, the multisystem sensor 10 may have an isolating portion 44 and one or more filters, reflective components, etc disposed between the sensor subsystems 14 and 16.

In one embodiment, the first cable 18 may communicate drive signals from the monitor 100 to the emitter 26 of the first sensor subsystem 14 and the emitter 30 of the second sensor subsystem 16. The second cable 22 may communicate signals generated by the detector 28 of the first sensor subsystem 14 and signals generated by the detector 32 of the second sensor subsystem 16. As both the emitters 26 and 30 and the detectors 28 and 32 are driven by a single monitor 100, the output generated by the detectors may be synchronized. In some embodiments, this may enable synchronization of monitoring of the first physiological characteristic by the first sensor subsystem 14 and monitoring of the second physiological characteristic measured by the second sensor subsystem 16. Alternatively, in other embodiments, each cable 18, 22 may each communicate separately with a respective sensor subsystem, i.e., cable 18 may allow communication between the monitor 100 and the first sensor subsystem 14, e.g., emitter 26 and detector 28, while cable 22 may allow communication between the monitor 100 and the second sensor subsystem 16, e.g., emitter 30 and detector 32.

Figure 12:
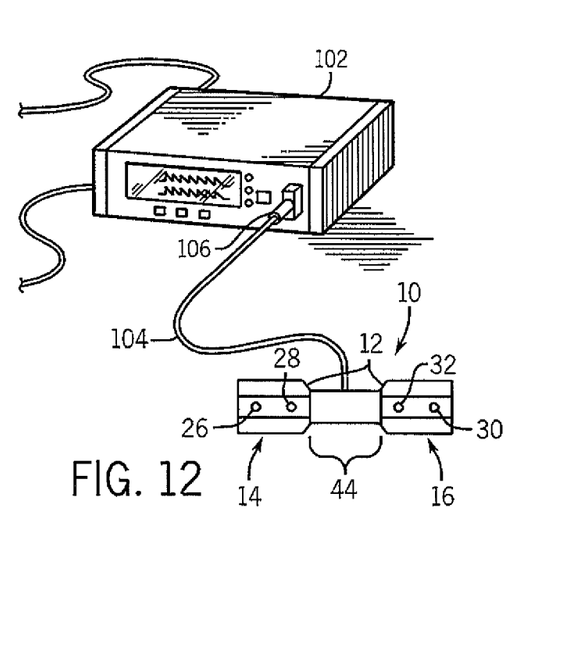
FIG. 12 depicts a multisystem sensor having a single cable coupled to a single monitor in accordance with another embodiment of the present disclosure.

FIG. 12 depicts an embodiment of the multisystem sensor 10 coupled to a single monitor 102 in accordance with another embodiment of the present disclosure. As described above, in one embodiment the multisystem sensor 10 may include a sensor body 12 housing a first sensor subsystem 14 and a second sensor subsystem 16. The first sensor subsystem 14 may include the emitter 26 and the detector 28 for determining a physiological characteristic of a patient. The second sensor subsystem 16 may include the emitter 30 and a detector 32 for determining a second physiological characteristic of a patient. As also discussed above in FIGS. 5-7, the multisystem sensor 10 may have an isolating portion 44 and one or more filters, reflective components, etc disposed between the sensor subsystems 14 and 16.

The sensor may be coupled to the monitor 102 by a single cable 104 and connector 106. In such an embodiment, both the first sensor subsystem 14 and the second subsystem 16 may communicate with the monitor 102 via the cable 104. The cable 104 may communicate multiple drive signals from the monitor 102 to the emitter 26 of the first sensor subsystem 14 and the emitter 30 of the second subsystem 16. The cable 104 may also communicate signals generated by the detectors 28 and 32 from the sensor 10 to the monitor 102. In some embodiments, the emitters 26 and 30 and the detectors 28 and 32 may be synchronized by the signals received from the monitor 102.

Figure 13:
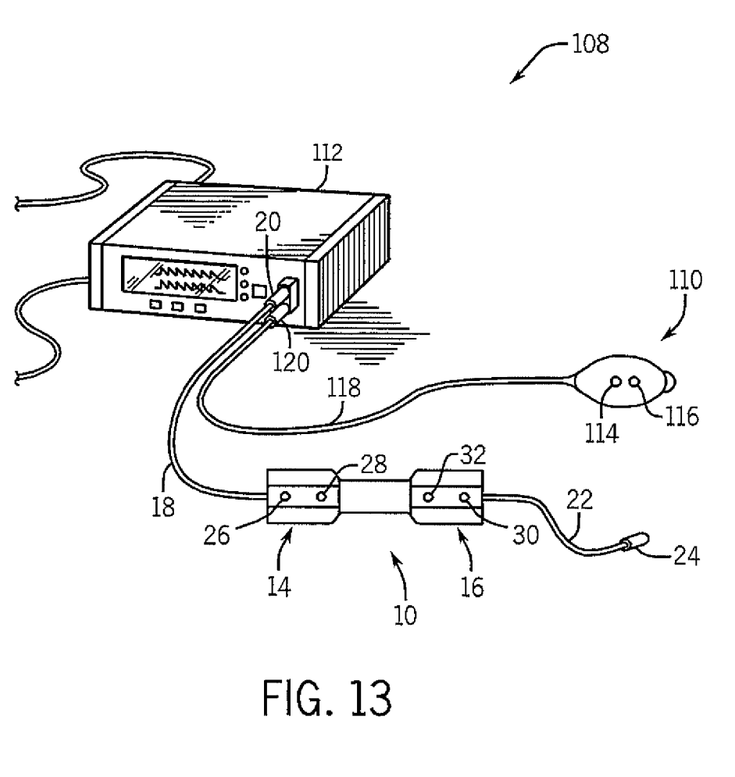
FIG. 13 depicts a medical monitoring system having the multisystem sensor of FIG. 1 and a second sensor in accordance with another embodiment of the present disclosure.

FIG. 13 depicts a medical monitoring system 108 having the multisystem sensor 10 and a second sensor 110 in accordance with another embodiment of the present disclosure. The multisystem sensor 10 may be used in conjunction with the second sensor 110 to derive a physiological characteristic of a patient, such that both the multisystem sensor 10 and the second sensor 110 are coupled to a monitor 112. The second sensor 110 may be any type of sensor suitable for use with either the first sensor subsystem 14 or second sensor subsystem 16 of the multisystem sensor 10. In one embodiment, as discussed above in FIG. 2, the second sensor 110 may be an optical sensor having an emitter 114 and detector 116 in a reflectance or transmittance configuration.

The first sensor subsystem 14 of the multisystem sensor 10 may be coupled to the monitor 112 via the cable 18 and connector 20. The second sensor may be simultaneously coupled to the monitor 112 via a sensor cable 118 and connector 120. During operation, the multisystem sensor 10 may be applied to a first sensor site on a patient and the second sensor 110 may be applied to a second sensor site on the patient. The monitor 112 may receive data from the first sensor subsystem 14 and from the second sensor 110 and determine a physiological characteristic of a patient based on a comparison between the data received from each respective sensor site. Additionally, as both the multisystem sensor 10 and the second sensor 110 are coupled to the monitor 112, the drive signals and signals generated by the detectors of each sensor may be synchronized. For example, in one embodiment, the multisystem sensor 10 and the second sensor 110 may provide differential pulse transit time (DPTT) data for use in determination of continuous non-invasive blood pressure (cNIBP). In some embodiments, the second sensor subsystem 16 may be coupled to a second monitor (via cable 22 and connector 24) so that the second sensor subsystem 16 may enable monitoring of another physiological characteristic of the patient, based on data measured at the first sensor site.

While the disclosure may be susceptible to various modifications and alternative forms, specific embodiments have been shown by way of example in the drawings and have been described in detail herein. However, it should be understood that the embodiments provided herein are not intended to be limited to the particular forms disclosed. Rather, the various embodiments may cover all modifications, equivalents, and alternatives falling within the spirit and scope of the disclosure as defined by the following appended claims.

What is claimed is:

1. A sensor comprising:
a single sensor body having a first surface configured to contact a patient when applied to the patient, comprising:
a first sensor subsystem disposed on the first surface of the sensor body, comprising:
a first emitter configured to emit light at one or more wavelengths;
a first detector configured to detect light at the one or more wavelengths;
a second sensor subsystem disposed on the first surface of the sensor body, comprising:
a second emitter configured to emit light at one or more wavelengths;
a second detector configured to detect light at the one or more wavelengths; and
an isolating portion separating the first sensor subsystem from the second sensor subsystem, wherein the isolating portion is disposed between the first sensor subsystem and the second sensor subsystem and forms a portion of the first surface of the sensor body and is configured to functionally isolate the first sensor subsystem from the second sensor subsystem when the first sensor subsystem and the second sensor subsystem are positioned on a common measurement surface.

2. The sensor of claim 1, wherein the first sensor subsystem is configured to determine a first physiological characteristic and the second sensor subsystem is configured to determine a second physiological characteristic.

3. The sensor of claim 2 wherein at least one of the first physiological characteristic or the second physiological characteristic comprises blood or tissue oxygenation and perfusion, respiratory rate, respiratory effort, continuous non-invasive blood pressure, cardiovascular effort, glucose level, level of consciousness, hematocrit, dysfunctional hemoglobin content, or hydration.

4. The sensor of claim 1, wherein the isolating portion comprises one or more filters configured to filter light emitted by one or both of the first emitter or the second emitter.

5. The sensor of claim 1, wherein the sensor body comprises one or more refractive components configured to attenuate light emitted from the first sensor subsystem before reaching the second sensor subsystem.

6. The sensor of claim 1, wherein the sensor body comprises a flexible portion configured to secure to a patient.

7. The sensor of claim 1, comprising a cable communicatively coupled to the first sensor subsystem and the second sensor subsystem.

8. The sensor of claim 1, comprising a first cable communicatively coupled to the first sensor subsystem.

9. The sensor of claim 1, comprising a wireless transceiver configured to transmit signals generated by the first sensor subsystem.

10. The sensor of claim 1, comprising a memory configured to store sensor identification, calibration information, or a combination thereof.

11. The sensor of claim 1, wherein the isolating portion is configured to maintain a minimal distance between the first and second sensor subsystems to functionally isolate the first sensor subsystem from the second sensor subsystem.

12. A sensor comprising:
a single sensor body having a first surface configured to contact a patient when applied to the patient, comprising:
a first sensor subsystem disposed on the first surface of the sensor body and configured to determine a first physiological characteristic, comprising:
a first emitter configured to emit light at one or more wavelengths;
a first detector configured to detect light at the one or more wavelengths;
a second sensor subsystem disposed on the first surface of the sensor body and configured to determine a second physiological characteristic, and
an isolating portion disposed between the first sensor subsystem and the second sensor subsystem, wherein the isolating portion forms a portion of the first surface of the sensor body and separating the first sensor subsystem from the second sensor subsystem and is configured to functionally isolate the first sensor subsystem from the second sensor subsystem when the first sensor subsystem and the second sensor subsystem are positioned on a common measurement surface.

13. The sensor of claim 12, wherein at least one of the first physiological characteristic or the second physiological characteristic comprises blood or tissue oxygenation and perfusion, respiratory rate, respiratory effort, continuous non-invasive blood pressure, cardiovascular effort, glucose level, level of consciousness, hematocrit, dysfunctional hemoglobin content, or hydration.

14. The sensor of claim 12, wherein the second sensor subsystem comprises an acoustic microphone or a transducer.

15. The sensor of claim 12, wherein the second sensor subsystem comprises a temperature sensor configured to measure an internal temperature or an external temperature of a patient.

16. The sensor of claim 12, wherein the second sensor subsystem comprises a pressure sensor configured to provide a signal representative of an attachment pressure of the sensor body to a patient's tissue.

17. The sensor of claim 12, wherein the second sensor subsystem comprises an electrical sensor, an electric probe, an electric lead, or an electric contact.

18. The sensor of claim 12, wherein the first sensor subsystem is communicatively coupled to a first monitor by a first cable, and wherein the second sensor subsystem is communicatively coupled to the first monitor by a second cable.

19. The sensor of claim 12, wherein the first sensor subsystem is communicatively coupled to a first monitor by a first cable, and wherein the second sensor subsystem is communicatively coupled to a second monitor by a second cable.

20. The sensor of claim 12, comprising a wireless transceiver configured to transmit signals generated by the first sensor subsystem or the second sensor subsystem.

21. The sensor of claim 20, wherein the wireless transceiver is configured to wirelessly communicate with a first monitor.

22. The sensor of claim 12, comprising a memory configured to store sensor identification, calibration information, or a combination thereof.

23. The sensor of claim 12, wherein the isolating portion is configured to maintain a minimal distance between the first and second sensor subsystems to functionally isolate the first sensor subsystem from the second sensor subsystem.

* * * * *